United States Patent
Geng et al.

(10) Patent No.: US 10,155,013 B2
(45) Date of Patent: Dec. 18, 2018

(54) PERIPLANETA AMERICANA EXTRACT OR PERIPLANETA AMERICANA MEDICINAL POWDER AS WELL AS PREPARATION METHOD THEREOF AND APPLICATION IN PREPARATION FOR MEDICINE USED FOR PREVENTING AND TREATING RADIATION-INDUCED DAMAGES

(71) Applicant: Sichuan Gooddoctor Panxi Pharmaceutical Co.,Ltd., Chengdu (CN)

(72) Inventors: Funeng Geng, Chengdu (CN); Guangjian Chen, Chengdu (CN)

(73) Assignee: Sichuan Gooddoctor Panxi Pharmaceutical Co., Ltd., Chengdu (CN)

( * ) Notice: Subject to any disclaimer, the term of this patent is extended or adjusted under 35 U.S.C. 154(b) by 29 days.

(21) Appl. No.: 15/193,182

(22) Filed: Jun. 27, 2016

(65) Prior Publication Data

US 2017/0000829 A1    Jan. 5, 2017

(30) Foreign Application Priority Data

Jun. 30, 2015  (CN) .......................... 2015 1 0375515
Jun. 21, 2016  (CN) .......................... 2016 1 0446370

(51) Int. Cl.
  *A61K 35/64*   (2015.01)
  *A61K 9/00*    (2006.01)
  *A61K 35/63*   (2015.01)

(52) U.S. Cl.
  CPC ............ *A61K 35/64* (2013.01); *A61K 9/0014* (2013.01); *A61K 9/0053* (2013.01); *A61K 35/63* (2015.01)

(58) Field of Classification Search
  CPC ..................................................... A61K 36/00
  See application file for complete search history.

(56) References Cited

FOREIGN PATENT DOCUMENTS

CN    101822696 A  *  9/2010
CN    102885857 A  *  1/2013

OTHER PUBLICATIONS

Luo et al: Enzymatic process of ethanol extract from Periplaneta americana by papain. Zhongguo Shiyan Fangjixue Zazhi (2012), 18(8), 15-17 (Year: 2012).*
Luo et al: Enzynnaticprocess of ethanol extract from Periplaneta americana by papain. Zhongguo ShiyanFangjixue Zazhi (2012), 18(8), 15-17 (Year: 2012) (Year: 2012).*

* cited by examiner

*Primary Examiner* — Qiuwen Mi
(74) *Attorney, Agent, or Firm* — Wayne & Ken, LLC; Tony Hom

(57) ABSTRACT

The present invention provides an application of a *periplaneta americana* medicinal powder or a *periplaneta americana* extract in preparation for a medicine used for preventing and treating radiation-induced damages. The medicine is capable of preventing and treating the damages caused by radiation therapy for nasopharyngeal cancer, esophageal cancer, stomach cancer, lung cancer, liver cancer, breast cancer, waldeyer's lymphoma, and other cancers. Through test verification, the medicine of the present invention has an obvious prevention and treatment effect for damages caused by radiation therapy for patients with breast tumors and breast cancer after surgery.

11 Claims, No Drawings

PERIPLANETA AMERICANA EXTRACT OR PERIPLANETA AMERICANA MEDICINAL POWDER AS WELL AS PREPARATION METHOD THEREOF AND APPLICATION IN PREPARATION FOR MEDICINE USED FOR PREVENTING AND TREATING RADIATION-INDUCED DAMAGES

CROSS-REFERENCE TO RELATED APPLICATIONS

This application claims foreign benefit from Chinese Patent Application No. 201510375515.4 with a filing date of Jun. 30, 2015 and No. 201610446370.7 with a filing date of Jun. 21, 2016. The content of the aforementioned applications, including any intervening amendments thereto, are incorporated herein by reference.

TECHNICAL FIELD

The present invention belongs to the field of medicine, and specifically relates to a *periplaneta americana* extract or a *periplaneta americana* medicinal powder as well as a preparation method thereof and an application in preparation for a medicine used for preventing and treating radiation-induced damages.

BACKGROUND OF THE PRESENT INVENTION

Radiation therapy is one of the most common therapy methods for malignant tumours, and most of patients with tumours need radiation therapy clinically. However, radioactive rays inevitably damage surrounding tissues and normal cells while killing tumour cells due to the obvious aggression thereof on human bodies, and poor specific selection function thereof for a tumour cell killing effect, thereby causing a series of systemic and local toxic and side reactions of the bodies; therefore, harms with different degrees are caused to the patients, both psychologically and physically.

The main side effects of radiation therapy comprise: (1) the damages of nasopharynxes, oral mucosae and skins; (2) the radioactive damages of hearts; (3) radioactive pneumonitis; (4) the radioactive damages of bone marrows; and (5) others: radioactive brain damages, radioactive proctitis, bladder damages and the like, wherein the damages of oral and nasal mucosae and skins will occur during the radiation therapy, and the patients will have the diseases of xerostomia and pharyngoxerosis, oral ulcers, skin pigmentation and the like, but some damages will occur within several weeks and even several months after the radiation therapy, for example, radioactive lung damages are divided into an early stage, a medium stage and a later stage. The early stage usually occurs within several weeks after radiation therapy, and is clinically presented as acute radioactive pneumonitis; and the later stage may occur within six months or longer after radiation.

Since radiation therapy brings about great harms to human bodies, modern medical workers are in urgent need of searching a biological agent for resolving the hazards of the radiation therapy and mitigating the pain of the human bodies.

*Periplaneta americana* is a *periplaneta* insect of blattidae of insecta *pterygota blattaria*, commonly known as 'cockroach', and only contained in the 'Sheng Nong's herbal classic' as a medicine, wherein the *periplaneta americana* is classified as a medium-grade medicine, called 'flavour: salty and cold; cure: cold and heat syndrome of blood stasis, accumulation breaking, hypopharynx atresia, and internal cold and childlessness'. 'Cockroach' is the common name of the *periplaneta americana*, first appeared in the 'Supplement to Compendium of Materia Medica', and also referred to as Shijiang and Huachong; and there are different names in various places, for example, Touyoupo, Chapozi, Zaomazi, and the like.

In recent years, as the emphasis on research and development of the traditional Chinese medicine resources in China, some scholars researched this injurious insect that cannot be eradicated for thousands of years in the aspect of applications, made gratifying achievements, and explored the positive value of this injurious insect in the traditional significance. A product 'Kangfuxin solution' made from a *periplaneta americana* alcohol extract through purification has a good curative effect on the wound surfaces of burns, scalds and other injuries, and is also capable of resisting inflammation, diminishing swelling, accelerating lesion tissue repair, and enhancing immunity; therefore, the product can be taken orally for treating duodenal ulcer, gastric ulcer and tuberculosis.

According to the modern digestion theory, proteins can only be absorbed by being converted to small molecular peptides through the gastrointestinal tract instead of being absorbed directly into the blood after being taken orally, the micromolecular peptides are mainly peptides containing 2-15 amino acid residues, with relative molecular masses of less than 3000, and the micromolecular peptides have the characteristics of being capable of being absorbed directly by the digestive tract, fast in transport speed, low in energy consumption, not liable to saturate, and the like. Main ingredients in the *periplaneta americana* alcohol extract further contain proteins, polypeptides and other macromolecular substances in addition to free amino acids, and the protein macromolecules can only play a corresponding role through the conversion of the gastrointestinal tract after being taken orally instead of being absorbed directly into the blood. Therefore, it is urgent for developing a novel *periplaneta americana* extract, and the main ingredients contained therein are free amino acids, peptides and other micromolecular substances that can be absorbed directly into the blood.

Currently, there is no application of a *periplaneta americana* medicinal powder and the extract thereof in radiation therapy.

SUMMARY OF PRESENT INVENTION

One objective of the present invention is to provide a *periplaneta americana* medicinal powder or a *periplaneta americana* extract.

Another objective of the present invention is to provide a preparation method for a *periplaneta americana* medicinal powder or a *periplaneta americana* extract.

A further objective of the present invention is to provide an application of a *periplaneta americana* medicinal powder or a *periplaneta americana* extract in a medicine used for preventing and treating radiation-induced damages.

In order to achieve the objectives, the present invention provides a *periplaneta americana* medicinal powder, a *periplaneta americana* extract as well as preparation methods thereof and an application in preparation for a medicine used for preventing and treating radiation-induced damages.

The medicine prepared in the present invention is capable of preventing and treating the skin damages caused by radiation therapy for nasopharyngeal cancer, esophageal cancer, stomach cancer, lung cancer, liver cancer, breast cancer, waldeyer's lymphoma, and other cancers.

The medicine of the present invention is a pharmaceutical preparation prepared by taking a *periplaneta americana* extract or a *periplaneta americana* medicinal powder as an active ingredient, and adding pharmaceutically common auxiliary materials; the pharmaceutical preparation may be an oral preparation or an external preparation; and the oral preparation comprises a liquid preparation, capsules, powder and tablets; and the external preparation comprises a gel, an ointment, a liquid preparation and cataplasm.

The medicine of the present invention may also be a *periplaneta americana* extract or a *periplaneta americana* medicinal powder directly.

Any preparation prepared from the *periplaneta americana* extract of the present invention meets the provisions on Kangfuxin (*periplaneta americana* extract) in standards with a number of WS3-B-3674-98, and is an extract of the dry insect bodies of *periplaneta americana*, with a total amino acid content of not less than 7.0%.

The *periplaneta americana* extract may also specifically refer to a *periplaneta americana* zymolyte.

The *periplaneta americana* extract may be prepared as Kangfuxin solution.

The objectives of the present invention are realized through the following technical solution:

firstly, the *periplaneta americana* extract (zymolyte) is realized through the following steps:

(1) taking the dry insects or fresh insects of *periplaneta americana*, crushing and then adding pure water with a weight which is 2 times to 20 times the weight of the raw material medicine, uniformly mixing the material solution, and regulating a pH value;

(2) adding protease with a weight which is 1% to 10% of the weight of the raw material medicine in the material solution in the step (1), hydrolyzing, then filtering, refrigerating, degreasing, and then centrifuging; concentrating the supernatant after centrifuging, adding ethanol in the concentrated solution until the volume concentration of ethanol in the obtained solution is 60% to 90%, standing, filtering, and recovering ethanol from the filtrate, so as to obtain a filtrate after ethanol recovery;

(3) taking the filtrate after ethanol recovery, which is obtained in the step (2), enabling the filtrate to pass through an adsorption resin column, washing the filtrate with pure water, and collecting an effluent until ninhydrin reaction of the effluent is negative; and then enabling the effluent to pass through a polyamide column, washing the effluent with pure water, and collecting an effluent until the ninhydrin reaction of the effluent is negative; and (4) concentrating and drying the final effluent obtained in the step (3) to obtain the *periplaneta americana* zymolyte.

Wherein, the weight of the pure water in the step (1) is 10 times to 20 times the weight of the raw material medicine.

Wherein, the protease in the step (2) is one or a combination of more than one of pepsin, trypsin, papain, neutral protease, chymotrypsin and elastase, wherein the adding amount of the protease is 3% to 10% of the weight of the raw material medicine.

Wherein, the hydrolysis temperature in the step (2) is 20° C. to 60° C.

Wherein, the hydrolysis time in the step (2) is 1 hour to 8 hours, and preferably 3.5 hours to 8 hours.

Wherein, the centrifuging time in the step (2) is 15 minutes to 60 minutes, and the rate is 10000 rev/min to 28000 rev/min.

Wherein, the volume concentration of the added ethanol in the step (2) is 90% to 96%.

Wherein, the standing temperature in the step (2) is ° C. to 10° C. and the standing time is 12 hours to 24 hours.

Wherein the adsorption resin column in the step (3) is a polar macroporous resin or a weakly polar macroporous resin or a non-polar macroporous resin.

Wherein the particle size of polyamide in the polyamide column in the step (3) is 100 meshes to 200 meshes.

The total amino acid content of the *periplaneta americana* extract is not less than 7.0%.

The peptide ingredient content of the *periplaneta americana* extract occupies 50% to 63% (percentage by weight).

Furthermore, the *periplaneta americana* medicinal powder is prepared through the following steps:

the *periplaneta americana* medicinal powder is prepared through the following steps:

(1) placing the dry insects or fresh insects of *periplaneta americana* in an ultralow-temperature crusher at a temperature set to −190° C. to −40° C. and crushing the dry insects or fresh insects to 100 meshes to 200 meshes;

(2) adding purified water with a weight which is 6 times to 10 times the weight of the raw medicinal material in the powdery *periplaneta americana* obtained in the step (1) and preparing a suspension, pouring the prepared suspension onto an ultrahigh-pressure homogenizer in an environment at 15° C. to 24° C., carrying out ultrahigh-pressure homogenizing for 10 minutes to 30 minutes at a pressure of 90 MPa to 130 MPa, and continuously carrying out the ultrahigh-pressure homogenizing for 3 to 4 cycles to prepare a homogenized solution;

(3) carrying out spray-drying on the homogenized solution obtained in the step (2) at 30° C. to 60° C. until a water content is 1% to 4%, so as to prepare a *periplaneta americana* powder; and (4) adding fumed silica with a weight which is 0.1% to 3% of the weight of the raw medicinal material in the *periplaneta americana* powder obtained in the step (3), and uniformly mixing to obtain a *periplaneta americana* medicinal powder.

Preferably, the *periplaneta americana* medicinal powder is realized through the following technical solution:

(1) placing the dry insects or fresh insects of *periplaneta americana* in an ultralow-temperature crusher at a temperature set to −170° C. to −160° and crushing the dry insects or fresh insects to 200 meshes;

(2) adding purified water with a weight which is 9 times the weight of the raw medicinal material in the powdery *periplaneta americana* obtained in the step (1) and preparing a suspension, pouring the prepared suspension onto an ultrahigh-pressure homogenizer in an environment at 20° C., carrying out ultrahigh-pressure homogenizing for 10 minutes to 15 minutes at a pressure of 90 MPa to 100 MPa, and continuously carrying out the ultrahigh-pressure homogenizing for 3 to 4 cycles to prepare a homogenized solution;

(3) carrying out spray-drying on the homogenized solution obtained in the step (2) at 35° C. until a water content is 1% to 3%, so as to prepare a *periplaneta americana* powder; and (4) adding fumed silica with a weight which is 0.5% to 2% of the weight of the raw medicinal material in the *periplaneta americana* powder obtained in the step (3), and uniformly mixing to obtain a *periplaneta americana* medicinal powder.

The medication mode of the medicine of the present invention is single use or co-use of an oral mode and an external mode.

Through test verification, the medicine of the present invention has an obvious curative effect in prevention and treatment for radiation-induced damages, and particularly has a great prevention and treatment effect on the skin damages caused by radiation therapy for patients with breast cancer after surgery; and the medicine of the present invention further has a great prevention and treatment effect on the radioactive pneumonitis and radioactive skin damages of patients with breast tumours.

The medicine of the present invention is further illustrated below in detail in the form of specific embodiments. However, it should not be understood that the scope of the above-mentioned subject matter of the present invention is merely limited to the following embodiments. The technologies realized on the basis of the contents of the present invention all fall into the scope of the present invention.

DETAILED DESCRIPTION OF PREFERRED EMBODIMENTS

Embodiment 1: *Periplaneta americana* Extract 1000 kg of the dried *periplaneta americana* is coarsely crushed, 4 times amount of 70% ethanol is added, the *periplaneta americana* is extracted twice at a temperature of 70° C. after being soaked for 1 hour, and the time of the first extraction is 8 hours; and 3 times amount of ethanol is added in the second time, the *periplaneta americana* is extracted for 6 hours, the two times of extraction solution is combined and filtered, and when the filtrate is concentrated into a clear paste with a relative density of 1.09 to 1.16 (70° Q, water is added, the clear paste is subjected to heat-insulation stirring for 60 minutes at 70° C. and stood for 12 hours, upper-layer fats are removed, the lower-layer medicinal solution is filtered, ethanol is recovered from the filtrate, and the filtrate is concentrated into a medicinal solution with a relative density of 1.16 to 1.22 (70° C.) under reduced pressure, so as to obtain the *periplaneta americana* extract.

Embodiment 2: *Periplaneta americana* Medicinal Powder 10 kg of the adult insects of *periplaneta americana* cultivated in a GAP base is weighed, placed in an ultralow-temperature crusher at a temperature set to −160° C. and crushed to 200 meshes; then 90 kg of purified water is added to prepare a suspension, the prepared suspension is poured onto an ultrahigh-pressure homogenizer in an environment at 20° C. ultrahigh-pressure homogenizing is carried out for 15 minutes at a pressure of 90 MPa, and the ultrahigh-pressure homogenizing is continuously carried out for 4 cycles to prepare a homogenized solution; spray-drying is carried out on the homogenized solution at 35° C., and after a water content is measured to be 2.7%, 0.1 kg of fumed silica is added, and uniformly mixed to obtain the *periplaneta americana* medicinal powder.

Through detection according to JY/T001-1996 'General Rules for Transmission Electron Microscopy', the particle sizes of 85% of particles in the obtained *periplaneta americana* medicinal powder are within a range of 20 nm to 80 nm, and completely meet the scademic regulations of nanoparticles.

The obtained *periplaneta americana* medicinal powder may be filled directly into capsules to prepare capsules containing the *periplaneta americana* medicinal powder.

Embodiment 3: *Periplaneta americana* Medicinal Powder 20 kg of the adult insects of *periplaneta americana* cultivated in a GAP base is weighed, placed in an ultralow-temperature crusher at a temperature set to −190° C. and crushed to 200 meshes; then 120 kg of purified water is added to prepare a suspension, the prepared suspension is poured onto an ultrahigh-pressure homogenizer in an environment at 15° C., ultrahigh-pressure homogenizing is carried out for 30 minutes at a pressure of 100 MPa, and the ultrahigh-pressure homogenizing is continuously carried out for 3 cycles to prepare a homogenized solution; spray-drying is carried out on the homogenized solution at 60° C., and after a water content is measured to be 3.1%, 5 g of fumed silica is added, and uniformly mixed to obtain the *periplaneta americana* medicinal powder.

Through detection according to JY/T001-1996 'General Rules for Transmission Electron Microscopy', the particle sizes of 85% of particles in the obtained *periplaneta americana* medicinal powder are within a range of 20 nm to 80 nm, and completely meet the scademic regulations of nanoparticles.

The obtained *periplaneta americana* medicinal powder may be filled directly into capsules to prepare capsules containing the *periplaneta americana* medicinal powder.

Embodiment 4: *Periplaneta americana* Medicinal Powder 10 kg of the adult insects of *periplaneta americana* cultivated in a GAP base is weighed, placed in an ultralow-temperature crusher at a temperature set to −40° C. and crushed to 100 meshes; then 100 kg of purified water is added to prepare a suspension, the prepared suspension is poured onto an ultrahigh-pressure homogenizer in an environment at 24° C., ultrahigh-pressure homogenizing is carried out for 10 minutes at a pressure of 130 MPa, and the ultrahigh-pressure homogenizing is continuously carried out for 4 cycles to prepare a homogenized solution; spray-drying is carried out on the homogenized solution at 30° C. and after a water content is measured to be 3.9%, 0.3 kg of fumed silica is added, and uniformly mixed to obtain the *periplaneta americana* medicinal powder.

Through detection according to JY/T001-1996 'General Rules for Transmission Electron Microscopy', the particle sizes of 85% of particles in the obtained *periplaneta americana* medicinal powder are within a range of 20 nm to 80 nm, and completely meet the scademic regulations of nanoparticles.

The obtained *periplaneta americana* medicinal powder may be filled directly into capsules to prepare capsules containing the *periplaneta americana* medicinal powder.

Embodiment 5: *Periplaneta americana* Medicinal Powder 5 kg of the adult insects of *periplaneta americana* cultivated in a GAP base is weighed, placed in an ultralow-temperature crusher at a temperature set to −170° and crushed to 200 meshes; then 40 kg of purified water is added to prepare a suspension, the prepared suspension is poured onto an ultrahigh-pressure homogenizer in an environment at 21° C. ultrahigh-pressure homogenizing is carried out for 20 minutes at a pressure of 110 MPa, and the ultrahigh-pressure homogenizing is continuously carried out for 3 cycles to prepare a homogenized solution; spray-drying is carried out on the homogenized solution at 55° C. and after a water content is measured to be 1.5%, 5 g of fumed silica is added, and uniformly mixed to obtain the *periplaneta americana* medicinal powder.

Through detection according to JY/T001-1996 'General Rules for Transmission Electron Microscopy', the particle sizes of 85% of particles in the obtained *periplaneta americana* medicinal powder are within a range of 20 nm to 80 nm, and completely meet the scademic regulations of nanoparticles.

The obtained *periplaneta americana* medicinal powder may be filled directly into capsules to prepare capsules containing the *periplaneta americana* medicinal powder.

Embodiment 6: *Periplaneta americana* Extract (Zymolyte)

10 kg of the fresh insects and fresh materials of *periplaneta americana* is weighed and treated into a homogenate by virtue of a high-speed tissue masher, then 100 liters of water is added and uniformly mixed, the pH value is adjusted to 7.8 by 10% sodium hydroxide, elastase with a weight which is 4% of the weight of the medicinal material is added and uniformly mixed, the solution is kept for 8 hours at a temperature of 20° C. placed in a refrigeration chamber and refrigerated for 16 hours, and after upper-layer fats are removed by virtue of filter paper, the solution is centrifuged for 15 minutes at a rotational speed of 28000; the supernatant is concentrated to a relative density of 1.20 at 60° C., ethanol with a volume concentration of 94% is added into the solution until the volume concentration of ethanol in the solution reaches 60%, and the solution is stood for 12 hours at 10° C. and filtered; ethanol is recovered from the filtrate, and water is added to reach 15 liters, and the solution is filtered; and the filtrate is enabled to pass through a HPD300-type macroporous adsorption resin column, the resin column is washed with pure water, the effluent is collected until ninhydrin reaction of the effluent is negative, then the effluent is enabled to pass through a polyamide column with a particle size of 100 meshes, the polyamide column is washed with pure water, the effluent is collected until the ninhydrin reaction of the effluent is negative, and the effluent is concentrated under reduced pressure and at 60° dried and crushed to obtain 0.71 kg of light yellow powder, that is, the *periplaneta americana* zymolyte.

The peptide ingredient content of the above-mentioned *periplaneta americana* zymolyte is finally measured to be 61.7% (percentage by weight) by a kjeldah method in combination with an amino acid analyzer.

Embodiment 7: *Periplaneta americana* Extract (Zymolyte)

10 kg of the fresh insects and fresh materials of *periplaneta americana* is weighed and treated into a homogenate by virtue of a high-speed tissue masher, then 20 liters of water is added, the pH value is adjusted to 1.0 by 10% HCL solution, pepsin with a weight which is 1% of the weight of the medicinal material is added and uniformly mixed, the solution is kept for 4 hours at a temperature of 40° C., placed in a refrigeration chamber and refrigerated for 24 hours, and after upper-layer fats are removed by virtue of filter paper, the solution is centrifuged for 60 minutes at a rotational speed of 10000; the supernatant is concentrated to a relative density of 1.10 at 60° C., ethanol with a volume concentration of 90% is added into the solution until the volume concentration of ethanol in the solution reaches 80%, and the solution is stood for 12 hours at 0° C. and filtered; ethanol is recovered from the filtrate, and water is added to reach 5 liters, and the solution is filtered; and the filtrate is enabled to pass through a D101-type macroporous adsorption resin column, the resin column is washed with pure water, the effluent is collected until ninhydrin reaction of the effluent is negative, then the effluent is enabled to pass through a polyamide column with a particle size of 100 meshes, the polyamide column is washed with pure water, the effluent is collected until the ninhydrin reaction of the effluent is negative, and the effluent is concentrated under reduced pressure and at 79° C., dried and crushed to obtain 0.56 kg of light yellow powder, that is, the *periplaneta americana* zymolyte.

The peptide ingredient content of the above-mentioned *periplaneta americana* zymolyte is finally measured to be 52.3% (percentage by weight) by a kjeldah method in combination with an amino acid analyzer.

Embodiment 8: *Periplaneta americana* Extract (Zymolyte)

5 kg of the dry insects of *periplaneta americana* is weighed and crushed into a powder, then 60 liters of water is added and uniformly mixed, the pH value is adjusted to 8.0 by 10% sodium hydroxide, trypsin with a weight which is 1% of the weight of the medicinal material and neutral protease with a weight which is 3% of the weight of the medicinal material are added and uniformly mixed, the solution is kept for 4 hours at a temperature of 40° C., placed in a refrigeration chamber and refrigerated for 12 hours, and after upper-layer fats are removed by filter paper, the solution is centrifuged for 35 minutes at a rotational speed of 26000; the supernatant is concentrated to a relative density of 1.08 at 60° C., ethanol with a volume concentration of 96% is added into the solution until the volume concentration of ethanol in the solution reaches 85%, and the solution is stood for 18 hours at 8° C. and filtered; ethanol is recovered from the filtrate, and water is added to reach 8 liters, and the solution is filtered; and the filtrate is enabled to pass through an NK2-type macroporous adsorption resin column, the resin column is washed with pure water, the effluent is collected until ninhydrin reaction of the effluent is negative, then the effluent is enabled to pass through a polyamide column with a particle size of 100 meshes, the polyamide column is washed with pure water, the effluent is collected until the ninhydrin reaction of the effluent is negative, and the effluent is concentrated under reduced pressure and at 75° C., dried and crushed to obtain 1.05 kg of light yellow powder, that is, the *periplaneta americana* zymolyte.

The peptide ingredient content of the above-mentioned *periplaneta americana* zymolyte is finally measured to be 60.2% (percentage by weight) by a kjeldah method in combination with an amino acid analyzer.

Embodiment 9: *Periplaneta americana* Extract (Zymolyte)

5 kg of the dry insects of *periplaneta americana* is weighed and crushed into a powder, then 50 liters of water is added and uniformly mixed, the pH value is adjusted to 7.8 by 10% sodium hydroxide, neutral protease with a weight which is 2% of the weight of the medicinal material, trypsin with a weight which is 1.5% of the weight of the medicinal material and papain with a weight which is 1% of the weight of the medicinal material are added and uniformly mixed, the solution is kept for 2 hours at a temperature of 40° C. placed in a refrigeration chamber and refrigerated for 24 hours, and after upper-layer fats are removed by filter paper, the solution is centrifuged for 30 minutes at a rotational speed of 21000; the supernatant is concentrated to a relative density of 1.10 at 60° C., ethanol with a volume concentration of 90% is added into the solution until the volume concentration of ethanol in the solution reaches 80%, and the solution is stood for 16 hours at 4° C. and filtered; ethanol is recovered from the filtrate, and water is added to reach 7 liters, and the solution is centrifuged; and the supernatant is enabled to pass through an HPD600-type macroporous adsorption resin column, the resin column is washed with pure water, the effluent is collected until ninhydrin reaction of the effluent is negative, then the effluent is enabled to pass through a polyamide column with a particle size of 200 meshes, the polyamide column is washed with pure water, the effluent is collected until the ninhydrin reaction of the effluent is negative, and the effluent is concentrated under reduced pressure and at 75°, dried and crushed to obtain 1.02 kg of light yellow powder, that is, the *periplaneta americana* zymolyte.

The peptide ingredient content of the above-mentioned *periplaneta americana* zymolyte is finally measured to be 57.3% (percentage by weight) by a kjeldah method in combination with an amino acid analyzer.

Embodiment 10: *Periplaneta americana* Extract (Zymolyte)

5 kg of the dry insects of *periplaneta americana* is weighed and crushed into a powder, then 100 liters of pure water is added and uniformly mixed, the pH value is adjusted to 8.0 by 10% sodium hydroxide, trypsin with a weight which is 3% of the weight of the medicinal material is added and uniformly mixed, the solution is kept for 3.5 hours at a temperature of 45° C., placed in a refrigeration chamber and refrigerated for 20 hours, and after upper-layer fats are removed by filter paper, the solution is centrifuged for 50 minutes at a rotational speed of 15000; the supernatant is concentrated to a relative density of 1.15 at 60° C., ethanol with a volume concentration of 95% is added into the solution until the volume concentration of ethanol in the solution reaches 75%, and the solution is stood for 24 hours at 20° C. and filtered; ethanol is recovered from the filtrate, and water is added to reach 10 liters, and the solution is filtered; and the filtrate is enabled to pass through an HPD400-type macroporous adsorption resin column, the resin column is washed with pure water, the effluent is collected until ninhydrin reaction of the effluent is negative, then the effluent is enabled to pass through a polyamide column with a particle size of 100 meshes, the polyamide column is washed with pure water, the effluent is collected until the ninhydrin reaction of the effluent is negative, and the effluent is concentrated under reduced pressure and at 75° C., dried and crushed to obtain 1.05 kg of light yellow powder, that is, the *periplaneta americana* zymolyte.

The peptide ingredient content of the above-mentioned *periplaneta americana* zymolyte is finally measured to be 58.1% (percentage by weight) by a kjeldah method in combination with an amino acid analyzer.

Embodiment 11: *Periplaneta americana* Extract Gel Preparation

Formula: the *periplaneta americana* extract gel preparation is composed of the following components in percentage by mass: 5% of the *periplaneta americana* extract prepared in the embodiment 2, 0.5% of carbomer, 0.3% of triethanolamine, 0.5% of potassium sorbate, 5% of propylene glycol, 2% of oleoyl polyoxyl-6 glycerides, and the balance water.

Preparation method: taking carbomer, adding an appropriate amount of purified water and swelling the carbomer into 1% solution for the future use; taking oleoyl polyoxyl-6 glycerides, adding propylene glycol and dissolving, then adding the remaining amount of water and stirring, continuing to add potassium sorbate and the *periplaneta americana* extract, and dissolving; and after the two solutions are mixed, slowly dropping triethanolamine, stirring to form a uniform gel, carrying out hot-pressing sterilization and then sterilely filling a proper container with the uniform gel to obtain the finished *periplaneta americana* extract gel preparation.

The technical solution of the present invention is further verified below through experimental cases.

Experimental Case 1: An Application of the Medicine of the Present Invention in Prevention for Radiation-Induced Skin Damages 1. Grouping 210 SD rats at 4 to 6 weeks of age are randomly divided into 7 groups in total, that is, a normal group, a model group, a control group, a test group 1, a test group 2, a test group 3 and a test group 4, each group comprises 30 rats, and except the rats in the normal group and the control group, hair on the hind legs of the rats in the other groups needs to be shaved off before tests, and normally fed for 2 days.

2. Test Methods

Normal group: normally feeding.
Model group: giving the same dose of normal saline, twice a day.
Control group: giving Corbrin capsules (Hangzhou Zhongmei Huadong Medicine Co., Ltd.), with a dose of 0.3 g/kg, preparing a medicinal powder into a medicinal solution with a corresponding concentration by virtue of normal saline, and keeping 10 ml of the medicinal solution for gavage, twice a day.
Test group 1: using the *periplaneta americana* medicinal powder of the embodiment 3, blending the *periplaneta americana* medicinal powder into a paste by virtue of normal saline, uniformly coating a gauze with the paste, and then applying the gauze coated with the *periplaneta americana* medicinal powder onto the right hind legs needing to be radiated, of rats, twice a day.
Test group 2: using the *periplaneta americana* medicinal powder of the embodiment 3, with a dose of 80 mg/kg, preparing the *periplaneta americana* medicinal powder into a medicinal solution with a corresponding concentration by virtue of normal saline, and keeping 10 ml of the medicinal solution for gavage for rats, twice a day.
Test group 3: using the *periplaneta americana* extract of the embodiment 1, coating a gauze with the *periplaneta*

*americana* extract in a dipping manner, and then applying the gauze onto the right hind legs needing to be radiated, twice a day.

Test group 4: using a commercially available Kangfuxin solution (produced by Sichuan Good Doctor Panxi Pharmaceutical Co., Ltd., with a batch number of 20150305), and while keeping 10 ml of the Kangfuxin solution for gavage, uniformly spraying the Kangfuxin solution onto a gauze, and applying the gauze onto the right hind legs needing to be radiated, of rats, twice a day. After the rats in the model group, the test group 1, the test group 2, the test group 3 and the test group 4 are continuously administered for 7 days before radiation, the movements of the rats (not anesthetized) are limited on a special fixture, the centres of the right hind legs are radiated by 60Coγ rays for 10 minutes in one process within a radiation area with a diameter of 3 cm respectively, a total absorbed dose is 15 Gy, and a dose rate is 1.5 Gy/min. The skin reactions of the rats are observed after the rats are radiated for 10 days.

3. Judgement Criteria

The judgement criteria of radioactive dermatitis are the classification criteria of WHO on acute radioactive skin damages: class I: skin pigmentation, followed by erythema; class II: dry skin peeling; class III: wet dermatitis, exudation, and blister formation, followed by erosion and excoriation; and class IV: skin ulcer.

4. Statistical Method

T-test is carried out on the data obtained through experiments by virtue of SPSS17.0 software, and $P<0.05$ indicates statistical significance.

5. Experiment Results

The specific experiment results are shown in Table 1:

TABLE 1

The degrees of the radiation-induced skin damages of rats

| | n | Normal | Class I | Class II | Class III | Class IV | Occurrence Rate (%) |
|---|---|---|---|---|---|---|---|
| Normal group | 30 | 30 | 0 | 0 | 0 | 0 | 0 |
| Model group | 30 | 0 | 0 | 0 | 18 | 12 | 100.0 |
| Control group | 30 | 3 | 0 | 11 | 10 | 9 | 90.0 |
| Test group 1 | 30 | 12 | 12 | 5 | 1 | 0 | 60.0 |
| Test group 2 | 30 | 10 | 13 | 5 | 2 | 0 | 66.7 |
| Test group 3 | 30 | 11 | 10 | 8 | 1 | 0 | 63.3 |
| Test group 4 | 30 | 15 | 7 | 8 | 0 | 0 | 50.0 |

It can be obtained from the results in Table 1 after statistical analysis that: through comparison among the control group, the 4 test groups and the model group, the occurrence rates of the skin damages of the rats have significant differences (P values are all less than 0.01), and have statistical significance; and through comparison between the 4 test groups and the model group, the occurrence rates of the skin damages of the rats have differences (P values are all less than 0.05), and have statistical significance.

In summary, the medicine of the present invention plays a prevention role on the skin damages after radiation to a certain extent in oral medication or external medication or oral and external combined medication; and it can be obtained according to the above-mentioned experiment results that the medicine has an obvious prevention effect, and has developable market value and significance.

Experimental Case 2: An Application Search of the Medicine of the Present Invention in Radiation Therapy for Tumour-Bearing Mice 1. Establishment of Nude Mouse Xenograft Model A cultured culture medium in a culture bottle basically overgrown with SGC-7901 gastric cancer cells on a bottle wall is removed, the culture bottle is washed twice with PBS solution, a few drops of 0.25% trypsin is added for digestion, the digested cells are sucked into a centrifugal tube and centrifuged for 6 minutes at a rotational speed of 600 r/min, the supernatant is removed, 3 ml of RPMI1640 culture medium without calf serum is added, blown, beat and uniformly mixed by a suction tube (an appropriate amount of counting cells is taken), and then centrifuged (for 6 minutes at a rotational speed of 600 r/min), the supernatant is removed, and then the serum-free RPMI1640 culture medium is added according to the number of $5\times10^6/0.2$ ml, that is, $2.5\times10^7$/ml, of cells subcutaneously inoculated in the right axilla of each nude mouse, for subcutaneous inoculation for the nude mouse. The prepared SGC-7901 gastric cancer cell suspension is dyed by virtue of trypan blue according to a viable cell number of greater than 95%, 0.2 ml of the SGC-7901 cell suspension is injected in the disinfected right axilla of each nude mouse of 80 nude mice (half male and half female, with weights of 18 g to 20 g), the tumour formation conditions of the mice are observed after 4 days, and modelling for all the 80 mice is successful.

2. Test Methods 2.1 Grouping 80 tumour-bearing mice are randomly divided into 8 groups (a model group, a control group, a test group 1, a test group 2, a test group 3, a test group 4, a test group 5 and a test group 6), each group comprises 10 mice, and administration modes are as follows:

Model group: giving the same dose of normal saline, twice a day.

Control group: giving Corbrin capsules (Hangzhou Zhongmei Huadong Medicine Co., Ltd.), with a dose of 0.3 g/kg, preparing a medicinal powder into a medicinal solution with a corresponding concentration by virtue of normal saline, and keeping 10 ml of the medicinal solution for gavage, twice a day.

Test group 1: using the *periplaneta americana* medicinal powder of the embodiment 4, with a dose of 80 mg/kg, preparing the *periplaneta americana* medicinal powder into a medicinal solution with a corresponding concentration by virtue of normal saline, and keeping 10 ml of the medicinal solution for gavage for mice, twice a day.

Test group 2: using a commercially available Kangfuxin solution (produced by Sichuan Good Doctor Panxi Pharmaceutical Co., Ltd., with a batch number of 20150305), and keeping 10 ml of the Kangfuxin solution for gavage, twice a day.

Test group 3: during radiation therapy for the tumour-bearing mice, applying a gauze sprayed with Kangfuxin solution (produced by Sichuan Good Doctor Panxi Pharmaceutical Co., Ltd., with a batch number of 20150305) in skin ranges under rays, twice a day.

Test group 4: using the *periplaneta americana* extract of the embodiment 9, coating a gauze with the *periplaneta americana* extract in a dipping manner, and during radiation therapy for the tumour-bearing mice, applying the gauze in skin ranges under rays, twice a day.

Test group 5: using the *periplaneta americana* medicinal powder of the embodiment 4, with a dose of 80 mg/kg, preparing the *periplaneta americana* medicinal powder into a medicinal solution with a corresponding concentration by virtue of normal saline, and keeping 10 ml of the medicinal solution for gavage; and during radiation therapy for the mice, applying a gauze coated with the *periplaneta americana* extract of the embodiment 9 in a dipping manner, in skin ranges subjected to radiation therapy, twice a day.

Test group 6: using the *periplaneta americana* medicinal powder of the embodiment 5, with a dose of 80 mg/kg, preparing the *periplaneta americana* medicinal powder into a medicinal solution with a corresponding concentration by virtue of normal saline, and keeping 10 ml of the medicinal solution for gavage; and during radiation therapy for the mice, applying a gauze coated with the *periplaneta americana* extract of the embodiment 10 in a dipping manner, in skin ranges subjected to radiation therapy, twice a day.

2.2 Method

Except the model group, the mice in the other groups are radiated once by 60Co rays on the 7th day and the 10th day respectively after administration, with a radiation dose of 8 Gy, and the mice are put to death by neck breaking on the 15th day.

3. Judgement Criteria

The judgement criteria of radioactive dermatitis are the classification criteria of WHO on acute radioactive skin damages: class I: skin pigmentation, followed by erythema; class II: dry skin peeling; class Ill: wet dermatitis, exudation, and blister formation, followed by erosion and excoriation; and class IV: skin ulcer.

Tumour inhibition rate=(the average tumour weight of the model group–the average tumour weight of the test groups)/the average tumour weight of the model group×100%.

4. Statistical Method

T-test is carried out on the data obtained through experiments by virtue of SPSS17.0 software, and $P<0.05$ indicates statistical significance.

5. Results

The specific experiment results are shown in Table 2:

According to the data in Table 2 above, in the test group 5 and the test group 6, administration therapy is carried out in an external and oral combined form, and compared with the control group, the tumour inhibition rates and the occurrence rates of the skin damages of the two groups are obviously higher than those of the control group (P values are both less than 0.01); in the test group 1 and the test group 2, administration therapy is carried out in an oral form, and compared with the control group, the tumour inhibition rates are higher than that of the control group (P values are both less than 0.05), and the occurrence rates of the skin damages are obviously higher than that of the control group; and in the test group 4 and the test group 5, administration is carried out in an external form, and compared with the control group, the occurrence rates of the radioactive skin damages are obviously higher than that of the control group (P values are both less than 0.05), and it is indicated that the medicine of the present invention has an effect of preventing and treating the radioactive skin damages in case of being externally administrated.

In summary, through medication for the nude mice before radiation therapy, after the radiation therapy, the occurrence rates of the skin damages of the nude mice are obviously lower than that of the control group of Corbrin capsules, and it is indicated that the medicine of the present invention has an effect of preventing and treating radioactive dermatitis; and through medication for the tumour-bearing mice before radiation therapy, after the radiation therapy, the tumour inhibition rates are higher than that of the control group of Corbrin capsules, and the occurrence rates of radioactive dermatitis are lower than that of the control group of Corbrin capsules, and it is further indicated that the medicine of the present invention has an effect of preventing and treating radioactive dermatitis, and has a remarkable curative effect.

Experimental Case 3: A Clinical Search of the Medicine of the Present Invention in Prevention and Treatment for the Side Effects of Radiation Therapy for Breast Cancer 1. Case Experiment Data 250 female patients with an average age of 45 to 75, 21 to 30 days after radical surgery or breast-conserving surgery for breast cancer are randomly divided into 5 groups: a

|   | Tumour weight/g ($\bar{x} \pm s$) | Tumour inhibition rate (%) | The degrees of skin damages after radiation therapy | | | | | Occurrence Rate (%) |
|---|---|---|---|---|---|---|---|---|
|   |   |   | Normal | Class I | Class II | Class III | Class IV |   |
| Model group | 1.43 ± 0.33 | — | 0 | 0 | 0 | 2 | 8 | 100.0 |
| Control group | 1.15 ± 0.21 | 16.26 | 1 | 0 | 2 | 4 | 3 | 90.0 |
| Test group 1 | 0.83 ± 0.19* | 32.52 | 3 | 2 | 3 | 2 | 0 | 70.0 |
| Test group 2 | 0.93 ± 0.16* | 24.39 | 3 | 4 | 2 | 1 | 0 | 80.0 |
| Test group 3 | 0.95 ± 0.21* | 20.32 | 2 | 3 | 4 | 1 | 0 | 80.0 |
| Test group 4 | 0.91 ± 0.24* | 26.02 | 3 | 5 | 2 | 0 | 0 | 70.0 |
| Test group 5 | 0.73 ± 0.12** | 40.65 | 4 | 3 | 3 | 0 | 0 | 60.0 |
| Test group 6 | 0.76 ± 0.16** | 38.21 | 3 | 5 | 2 | 0 | 0 | 70.0 |

Note:
compared with the control group, **$P < 0.01$, and *$P < 0.05$ control group comprising 50 patients, specifically, 42 patients after radical surgery and 8 patients after breast-conserving surgery; an experiment group A comprising 50 patients, specifically, 39 patients after radical surgery and 11 patients after breast-conserving surgery; an experiment group B comprising 50 patients, specifically, 43 patients after radical surgery and 7 patients after breast-conserving surgery; an experiment group C comprising 50 patients, specifically, 40 patients after radical surgery and 10 patients after breast-conserving surgery; and an experiment group D comprising 50 patients, specifically, 38 patients after radical surgery and 12 patients after breast-conserving surgery. The general data comparison differences of the 5 groups have no statistical significance (P>0.05), and are comparable.

The 5 groups of patients are subjected to common chest wall and clavicle radiation. Mixed radiation is carried out by virtue of 6 MV high-energy X rays and 6 MeV to 10 MeV electron rays of a SIEMENS electron accelerator, with a radiation dose of 50 Gy/5 weeks.

2. Judgement Criteria

Radioactive dermatitis is classified according to the classification criteria of RTOG acute radioactive damages, and the classification criteria of the RTOG acute radioactive damages comprise 5 classes in total: class 0: basically no change; class I: blisters, light red flecks, hair loss, dry peeling, and sweating reduction; class II: skin touch-pain, obvious red flecks and flaky moist peeling, and moderate edema; class III: confluent moist peeling out of skin folds, and severe edema; and class IV: ulcer, bleeding, and necrosis.

3. Methods

Experiment group A: taking the *periplaneta americana* medicinal powder prepared in the embodiment 2 after dissolving with warm water everyday from the first day of radiation therapy, 5 g each time and thrice a day.

Experiment group B: taking Kangfuxin solution (produced by Sichuan Good Doctor Panxi Pharmaceutical Co., Ltd., with a batch number of 20150305) everyday from the first day of radiation therapy, 10 ml each time and thrice a day.

Experiment group C: applying a gauze sprayed with Kangfuxin solution (produced by Sichuan Good Doctor Panxi Pharmaceutical Co., Ltd., with a batch number of 20150305) onto parts needing radiation therapy everyday from the first day of radiation therapy, thrice a day.

Experiment group D: coating a gauze with the *periplaneta americana* extract of the embodiment 1 in a dipping manner, and then applying the gauze onto parts needing radiation therapy everyday from the first day of radiation therapy, thrice a day.

Control group: giving common skin care from the first day of radiation therapy, keeping skins in radiation fields clean and dry, and avoiding wiping with rough towels, random applying of ointments or lotions, contact with ethanol, iodine tincture, soap and the like, cold-hot stimulation, and exposure to the hot sun; keeping clothes loose and soft, and avoiding collar friction; and suspending the radiation therapy when skin damages reach class III and class IV, and treating until the skin damages are healed and then carrying out the radiation therapy.

The occurrence rates of radioactive skin damages=(1−(the number of class−0 cases/50)×100%

4. Statistical Method $x2$ inspection is carried out on the occurrence rates and occurrence degrees of the radioactive skin damages of the 4 experiment groups and the control group respectively by virtue of SPSS20.0.

5. Results

The comparison results of the skin damages with different degrees of the patients in the 4 groups are shown in Table 2:

TABLE 2

| Comparison (n) of the degrees of the radioactive skin damages of the 5 groups | | | | | | | | |
|---|---|---|---|---|---|---|---|---|
| | n | Class 0 | Class I | Class II | Class III | Class IV | Occurrence rate | $x2$ | P value |
| Control group | 50 | 0 | 20 | 18 | 8 | 4 | 100.0% | — | — |
| Experiment group A | 50 | 27 | 13 | 7 | 3 | 0 | 46.0% | 39.598 | 0.000 |
| Experiment group B | 50 | 23 | 16 | 9 | 2 | 0 | 54.0% | 34.044 | 0.000 |
| Experiment group C | 50 | 29 | 12 | 8 | 1 | 0 | 42.0% | 44.291 | 0.000 |
| Experiment group D | 50 | 30 | 13 | 5 | 2 | 0 | 40.0% | 46.433 | 0.000 |

Note:
$x2$ indicates a chi-square value obtained through comparison with the control group; and the P value indicates the P value obtained through comparison with the control group It can be obtained from the data in Table 2 that: the occurrence rates of the radioactive skin damages of the patients in the 4 experiment groups are obviously lower than the occurrence rate of the radioactive skin damages of the patients in the control group, P values are all less than 0.01, and the data has remarkable statistical significance. It is illustrated according to the experiment that the medicine of the present invention plays an obvious prevention and treatment role on the radioactive skin damages.

Experimental Case 4: A Clinical Research of the Medicine of the Present Invention in Prevention and Treatment for the Side Effects of Radiation Therapy for Chest Tumour 1. Case Experiment Data 160 patients with chest tumours, specifically, 75 patients with lung cancer and 85 patients with esophagus cancer, are selected, with an average age of 55 to 80, simultaneous application for patients subjected to radiation therapy and fasting are avoided in case selection, the cases are randomly divided into a control group, a test group 1, a test group 2 and a test group 3, each group comprises 40 patients, wherein the pathological types of the control group comprise 18 cases of lung cancer and 22 cases of esophagus cancer, and an average radiation dose is (63.56±8.17) Gy; the pathological types of test group 1 comprise 20 cases of lung cancer and 20 cases of esophagus cancer, and an average radiation dose is (58.23±7.11) Gy; the pathological types of test group 2 comprise 19 cases of lung cancer and 21 cases of esophagus cancer, and an average radiation dose is (65.89±10.32) Gy; the pathological types of test group 3 comprise 18 cases of lung cancer and 22 cases of esophagus cancer, and an average radiation dose is (64.77±6.54) Gy. The genders, ages, disease entities and radiation doses of the patients in the 4 groups are comparable through statistical analysis.

2. Methods

The patients in the 4 groups are all subjected to chest radiation therapy by virtue of 6 MV high-energy X rays and 6 MeV to 10 MeV electron rays of a SIEMENS electron accelerator, with a dose of 40 Gy to 70 Gy, and 1.8 Gy/F to 2.0 Gy/F. The radiation field of each breast primary lesion is 60 cm2 to 1636 cm2 (mantle field), and the treatment course of the radiation therapy is 30 days to 80 days. Treatment planning is carried out on most of the cases by virtue of a TPS (Treatment Planning System). The critical organs are shielded by virtue of a lead block technology or a wedge-shaped plate technology. The administration modes for the patients in the 4 groups are as follows:

Control group: commonly treating.

Test group 1: except the mode of commonly treating, taking the *periplaneta americana* medicinal powder of the embodiment 3 after dissolving with warm water everyday from the first day of radiation therapy, 5 g each time and thrice a day.

Test group 2: except the mode of commonly treating, coating a gauze with the *periplaneta americana* extract of the embodiment 6 in a dipping manner, and then applying the gauze onto parts under rays everyday from the first day of radiation therapy, thrice a day.

Test group 3: except the mode of commonly treating, orally taking the *periplaneta americana* medicinal powder of the embodiment 3 (in a taking mode the same as the test group 1) and externally applying the *periplaneta americana* extract of the embodiment 1 (in a using mode the same as the test group 2), thrice a day.

3. Diagnostic Criteria 3.1 Diagnostic Criteria of Radioactive Dermatitis

Radioactive dermatitis is classified according to the classification criteria of RTOG acute radioactive damages, and the classification criteria of RTOG acute radioactive damages comprise 5 classes in total: class 0: basically no change; class I: blisters, light red flecks, hair loss, dry peeling, and sweating reduction; class II: skin touch-pain, obvious red flecks and flaky moist peeling, and moderate edema; class III: confluent moist peeling out of skin folds, and severe edema; and class IV: ulcer, bleeding, and necrosis.

3.2 Diagnostic Criteria of Radioactive Pneumonitis

The diagnostic criteria of radioactive pneumonitis are the 'Diagnostic Criteria of Acute Radioactive Pneumonitis' (GBZ110-2002) in the national hygienic standards issued by the ministry of health;

(1) a lung radiation dose is more than 8 Gy (including 8 Gy);

(2) the patients have the clinical symptoms of cough, chest distress, chest pain, dyspnea, low-grade fever and so on;

(3) signs: the patients in less severe cases may have no obvious abnormalities, and the patients in severe cases have breath sound lowering, and dry and moist rales;

(4) it is found through X-ray examination that meshy and irregular-edge fuzzy shadows occur on the radiated lungs, or it is found through CT scanning that ground glass-like changes and patchy high-density shadows occur.

4. Statistical Method

T-test is carried out on the data obtained through experiments by virtue of SPSS17.0 software, and P<0.05 indicates statistical significance.

5. Results 5.1 The influence results of the medicine of the present invention on the occurrence rates of radioactive dermatitis in radiation therapy are shown in Table 4:

|  | Case number | Class 0 | Class I | Class II | Class III | Class IV | Occurrence rate (%) |
|---|---|---|---|---|---|---|---|
| Control group | 40 | 0 | 0 | 15 | 13 | 12 | 100.0 |
| Test group 1 | 40 | 17 | 9 | 13 | 1 | 0 | 57.5 |
| Test group 2 | 40 | 20 | 12 | 8 | 0 | 0 | 50.0 |
| Test group 3 | 40 | 24 | 9 | 7 | 0 | 0 | 40.0 |

It can be obtained from Table 4 that, compared with the control group, in the 3 test groups using the medicine of the present invention, the occurrence rates of radioactive dermatitis can be obviously reduced after radiation therapy for the patients with chest tumours, and the data has statistical significance (P<0.01).

5.2 The influence results of the medicine of the present invention on the occurrence rates of radioactive pneumonitis in radiation therapy are shown in Table 5:

|  | Control group | Test group 1 | Test group 2 | Test group 3 |
|---|---|---|---|---|
| Case number (n) | 40 | 40 | 40 | 40 |
| The number of radioactive pneumonitis cases | 26 | 6 | 8 | 4 |
| The occurrence rate of radioactive pneumonitis (%) | 65.0 | 15.0 | 20.0 | 10.0 |

It can be obtained from Table 5 that, compared with the control group, in the 3 test groups using the medicine of the present invention, the occurrence rates of radioactive pneumonitis can be obviously reduced after radiation therapy for the patients with chest tumours, and the data has statistical significance (P<0.01).

In summary, the medicine of the present invention plays an obvious prevention and treatment role on the side effects after radiation therapy, and particularly has a remarkable effect on reduction for the occurrence rates of the skin damages of patients with breast cancer and cured through surgery after radiation therapy, and the radioactive dermatitis and radioactive pneumonitis of the patients with breast tumours after radiation therapy.

The Kangfuxin solution of the present invention is produced by Sichuan Good Doctor Panxi Pharmaceutical Co., Ltd., is an extract of the dry insect bodies of *periplaneta americana*, and meets the standard provisions on Kangfuxin solution in WS3-B-3674-98.

We claim:

1. A *periplaneta americana* extract, wherein the *periplaneta americana* extract is a *periplaneta americana* zymolyte having a peptide content of 50-63% of total weight; and the *periplaneta americana* extract is prepared through the following steps:
   (1) crushing dry or fresh *periplaneta americana*; adding pure water 2-20 times the weight of the *periplaneta americana* to the *periplaneta americana*; uniformly mixing the pure water and the *periplaneta americana* to produce a mixture and regulating pH of the mixture;
   (2) adding protease of 1-10% of the weight of the *periplaneta americana* in the mixture obtained in step (1) to hydrolyze at 20-60° C. for 1-8 hours; subjecting the hydrolyzed mixture to filtration, refrigeration, degreasing and centrifugation to produce a supernatant; concentrating the supernatant to produce a concentrated solution; adding 90-96 vol. % ethanol in the concentrated solution to stand at 0-10° C. for 12-24 hours until a concentration of ethanol in the concentrated solution is 60-90% by volume; and then filtering the concentrated solution to produce a filtrate and recovering ethanol from the filtrate;
   (3) allowing the filtrate after ethanol recovery obtained in step (2) to pass through a resin column; washing the filtrate with pure water to collect a liquid until ninhydrin reaction of the liquid is negative; and then allowing the liquid to pass through a polyamide column; washing the liquid with pure water to collect an effluent until ninhydrin reaction of the effluent is negative; and
   (4) concentrating and drying the effluent obtained in step (3) to produce the *periplaneta americana* zymolyte.

2. The *periplaneta americana* extract of claim 1, wherein the *periplaneta americana* extract comprises a total amino content of 7.0% or more.

3. The *periplaneta americana* extract of claim 1, wherein the pure water in step (1) is 10-20 times the weight of the *periplaneta americana*.

4. The *periplaneta americana* extract of claim 1, wherein the protease in step (2) is at least one of pepsin, trypsin, papain, neutral protease, chymotrypsin and elastase.

5. The *periplaneta americana* extract of claim 1, wherein a hydrolysis time in step (2) is 3.5-8 hours.

6. The *periplaneta americana* extract of claim 1, wherein the centrifugation in step (2) is performed at a rate of 10000-28000 r/min for 15-60 minutes.

7. The *periplaneta americana* extract of claim 1, wherein the resin column in step (3) is selected from a polar macroporous resin, a weak-polar macroporous resin or a non-polar macroporous resin.

8. The *periplaneta americana* extract of claim 1, wherein the polyamide column in step (3) has a particle size of 100-200 mesh.

9. An application of the *periplaneta americana* extract of claim 1 in preparation of a medicine for preventing and treating radiation-induced damages.

10. The application of claim 9, wherein the medicine is used for preventing and treating the damages caused by radiation therapy for one or more of nasopharyngeal cancer, esophageal cancer, stomach cancer, lung cancer, liver cancer, breast cancer and waldeyer's lymphoma.

11. The application of claim 9, wherein the medicine is a pharmaceutical preparation comprising the *periplaneta americana* extract and auxiliaries; and the pharmaceutical preparation is selected from an oral preparation or an external preparation;
   wherein the oral preparation comprises a liquid preparation, capsules, powder and tablets; and
   the external preparation comprises a gel, an ointment, a liquid preparation and cataplasm.

* * * * *